(12) United States Patent
Saettel et al.

(10) Patent No.: US 9,010,477 B2
(45) Date of Patent: Apr. 21, 2015

(54) IN VEHICLE GLUCOSE APPARATUS AND VEHICULAR OPERATION INHIBITOR

(71) Applicants: Catherine Mary Saettel, Springboro, OH (US); Anthony Joseph Saettel, Springboro, OH (US); John Saettel, Springboro, OH (US)

(72) Inventors: Catherine Mary Saettel, Springboro, OH (US); Anthony Joseph Saettel, Springboro, OH (US); John Saettel, Springboro, OH (US)

(73) Assignee: AoneC, LLC, Springboro, OH (US)

( * ) Notice: Subject to any disclaimer, the term of this patent is extended or adjusted under 35 U.S.C. 154(b) by 0 days.

(21) Appl. No.: 13/767,974

(22) Filed: Feb. 15, 2013

(65) Prior Publication Data

US 2013/0217990 A1 Aug. 22, 2013

Related U.S. Application Data

(60) Provisional application No. 61/599,765, filed on Feb. 16, 2012.

(51) Int. Cl.
*B60K 28/06* (2006.01)
*A61B 5/145* (2006.01)
*F16H 61/22* (2006.01)
*A61B 5/00* (2006.01)

(52) U.S. Cl.
CPC ....... *A61B 5/14532* (2013.01); *F16H 2061/223* (2013.01); *B60K 28/06* (2013.01); *A61B 2503/22* (2013.01); *A61B 5/745* (2013.01); *B60W 2540/26* (2013.01)

(58) Field of Classification Search
CPC .... B60K 28/06; B60R 25/007; B60R 25/008; B60R 25/005; B60R 25/003; B60R 25/002; B60R 25/00; B60W 2540/26; B60W 2040/0818; A61B 2560/045; G01N 33/66; F16H 2061/223
USPC ............. 180/272, 271, 336; 340/576; 701/45, 701/36, 1
See application file for complete search history.

(56) References Cited

U.S. PATENT DOCUMENTS

| | | | |
|---|---|---|---|
| 3,977,488 A | 8/1976 | Kameyama | |
| 6,927,671 B2 | 8/2005 | DeBono | |
| 7,002,477 B1 * | 2/2006 | Camhi | ........................ 340/573.1 |
| 8,207,860 B2 | 6/2012 | Enegren et al. | |
| 2008/0015422 A1 * | 1/2008 | Wessel | .......................... 600/301 |

(Continued)

OTHER PUBLICATIONS

Definition of "immobilize"—http://www.merriam-webster.com/dictionary/immobilize.*

(Continued)

*Primary Examiner* — Keith Frisby
(74) *Attorney, Agent, or Firm* — Carin R. Miller; Thomas | Horstemeyer, LLP

(57) ABSTRACT

When diabetics undergo a hyperglycemic or hypoglycemic event, their cognitive-motor function can be severely impaired. This has contributed to a positive correlation between diabetes and traffic incidences. Disclosed herein are devices and methods for controlling a motor vehicle in response to a blood glucose concentration of an operator. In one embodiment, a motorized vehicle control apparatus contains a processer that determines if a received blood glucose concentration is within a predetermined range and a transmitter transmits a signal to immobilize a motor vehicle without disabling ignition in response to determining if a received blood glucose concentration is within a predetermined range.

14 Claims, 6 Drawing Sheets

(56) References Cited

U.S. PATENT DOCUMENTS

2008/0314116 A1* 12/2008 Leddy et al. .................. 73/23.3
2011/0178382 A1 7/2011 Topp

OTHER PUBLICATIONS

Chronic Medical Conditions and Traffic Safety-Review of the California Experience. J.A. Waller. New England J. Med., 1965; 273:1413-1420.
Driving with Diabetes in the Future: In-Vehicle Medical Monitoring. D. Kerr and T. Olateju. J. Diabetes Science and Technology, 2010: 4(2): 464-469.
ADA Diabetes Care Survey: Diabetes and Driving Mishaps, Frequency and Correlations from a multinational survey. D.J. Cox et al. Aug. 2003, vol. 26 (8): 2329-2334, published by the American Diabetes Association.
Driver Fitness Medical Guidelines published by the U.S. National Highway Traffic Safety Administration in cooperation with the American Association of Motor Vehicle Administrators, Sep. 2009.
Diabetes and Driving. D.M. Alexander, et al. Diabetes Care, 2006, vol. 29(8): 1942-1949.
National diabetes fact sheet: national estimates and general information on diabetes and prediabetes in the United States, 2011. Atlanta, GA: U.S. Department of Health and Human Services, Centers for Disease Control and Prevention, 2011. Published by the U.S. Department of Health and Human Services, Centers for Disease Control and Prevention.

* cited by examiner

IN VEHICLE GLUCOSE APPARATUS AND VEHICULAR OPERATION INHIBITOR

CROSS-REFERENCE TO RELATED APPLICATIONS

This application claims the benefit of U.S. provisional patent application Ser. No. 61/599,765, filed Feb. 16, 2012, having the title In Vehicle Glucose Monitor and Vehicle Control, which is incorporated herein by reference in its entirety.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION BY REFERENCE OF MATERIAL SUBMITTED ON A COMPACT DISC

Not Applicable

BACKGROUND

1. Technical Field

The present disclosure relates generally to blood glucose monitoring for improved diabetes control and, more specifically, for control of motor vehicle operation in response to blood glucose concentration.

2. Description of the Related Art

Diabetes is an endocrine disorder marked by an inability to produce or respond appropriately to insulin. If left uncontrolled, diabetes results in dysregulation of blood glucose and subsequently, hypoglycemia (low blood glucose concentration) or hyperglycemia (high blood glucose concentration). Effects of hypoglycemia and hyperglycemia include physiological impairments, coma, and death. Therefore, one aspect of a diabetes treatment regimen is monitoring blood glucose concentration throughout a day. However, not all diabetics test their blood glucose concentration frequently enough to prevent the effects of hypoglycemia and hyperglycemia. Thus, there are ongoing efforts to improve blood glucose concentration monitoring by diabetics.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE EMBODIMENTS

Figure 1:
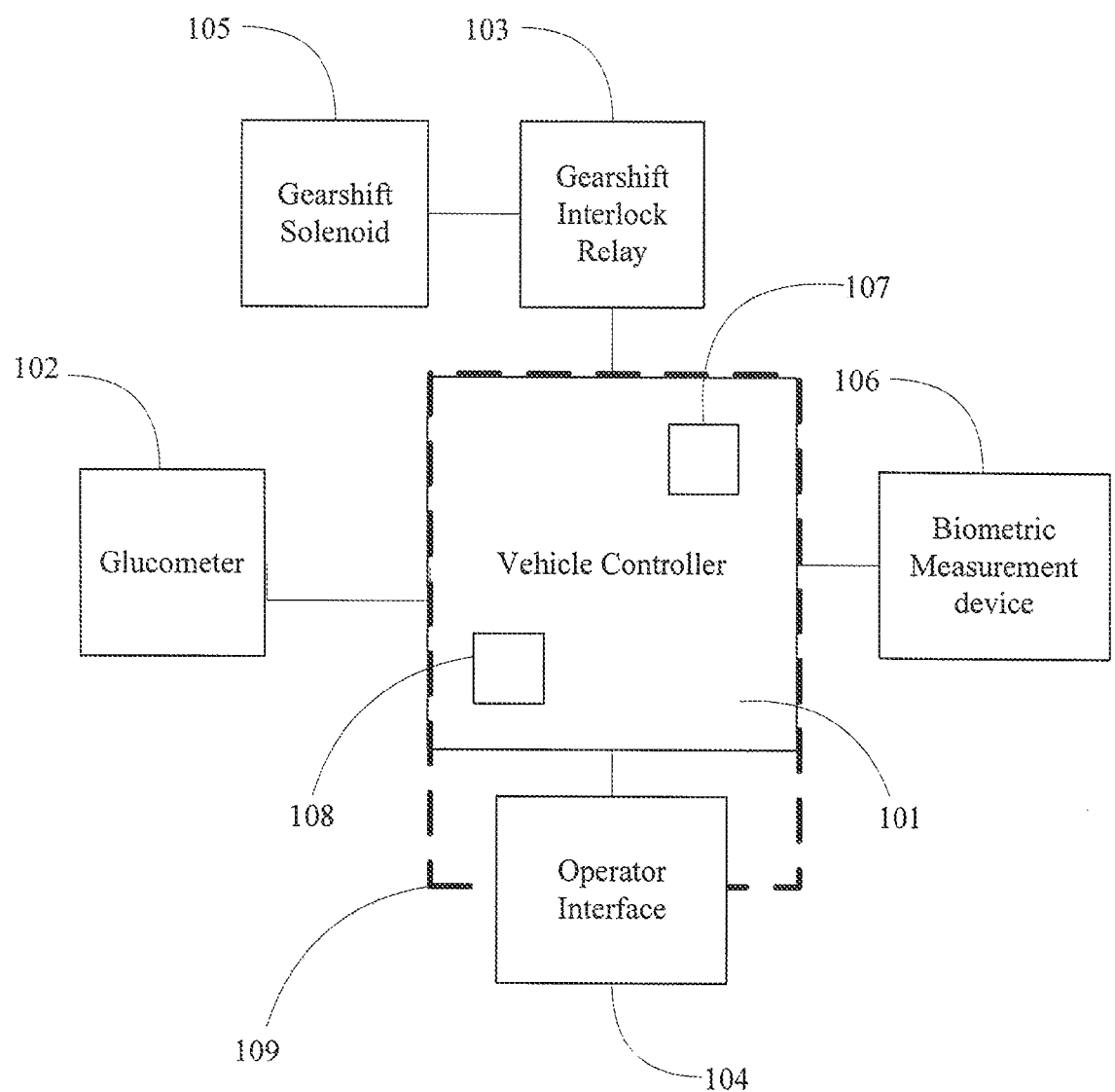
FIG. 1 shows one embodiment of an in-vehicle blood glucose-monitoring apparatus and motor vehicle operation control system.

Diabetes is a serious medical condition afflicting millions of people and is characterized by an inability to regulate blood glucose concentration appropriately. Type 1 diabetes is defined by a lack of insulin, while Type 2 diabetes is defined by insulin insensitivity. Both types, if not properly monitored and treated accordingly, can result in a blood glucose concentration that is too great (hyperglycemia) or too low (hypoglycemia). Although hypoglycemia is more common, as it is often a result of insulin therapy, both conditions are life-threatening to a diabetic. Hyperglycemia leads to ketoacidosis, which, if left untreated, results in coma and death. Hypoglycemia results in an immediate release of hormones like glucagon, epinephrine, growth hormone, and cortisol. These hormones contribute to a typical hypoglycemic reaction, which include physiologic symptoms such as blurred vision, confusion, weakness, dizziness, and lethargy. If left unnoticed and untreated, hypoglycemia can rapidly result in seizure, coma, and death.

Suffice it to say, diabetics are at risk for developing physiological symptoms that can severely impair, without notice, an ability to complete ordinary activities, such as operating a motorized vehicle. As early as four decades ago, a positive correlation between diabetes and increased motorized vehicle accidents and traffic violations was reported. See New England J. Med., 1965; 273:1413-1420, which is herein incorporated by reference in its entirety. Indeed, diabetes (Type 1 and Type 2) accounts for 18% of traffic accidents that are attributed to a medical condition in the United States (U.S.) and Europe. See J. Diabetes Science and Technology, 2010: 4(2): 464-469, which is herein incorporated by reference in its entirety. This is more than double an amount of accidents attributed to heart attack or stroke alone or combined. As compared with non-diabetics, Type 1 diabetic drivers are involved in almost three times more car accidents. Similarly, Type 2 diabetic drivers are one and a half times more likely to be involved in a car accident compared to non-diabetics. See ADA Diabetes Care Survey: Diabetes and Driving Mishaps, Frequency and Correlations from a multi-national survey, August 2003, Vol. 26 (8): 2329-2334, which is herein incorporated by reference in its entirety. Overall, diabetics have a 19% greater likelihood to be involved in a motor vehicle accident as compared to non-diabetics. See the Driver Fitness Medical Guidelines published by the U.S. National Highway Traffic Safety Administration in cooperation with the American Association of Motor Vehicle Administrators, September 2009, which is herein incorporated by reference in its entirety.

Moreover, hypoglycemia is identified as being a major risk factor for the observed increased likelihood of motor vehicle accidents by diabetics. With the physiological symptoms of hypoglycemia in mind, it is easy to appreciate that hypoglycemia is typically associated with an inability to maintain proper control of a motor vehicle. For example, hypoglycemia can result in increased swerving, lane changes, run-offs, spin-outs, and dangerously slow rates of driving speed. Strikingly, 31% of Type 1 diabetic U.S. drivers admit to driving in a hypoglycemic stupor. See Diabetes Care, 2006, Vol. 29(8): 1942-1949, which is herein incorporated by reference in its entirety. Hypoglycemic unawareness, or an inability to recognize or experience warning signs of hypoglycemia, is prevalent in approximately 25% of Type 1 diabetics. This equates to almost 1 million U.S. drivers. See Diabetes Care, 2006, Vol. 29(8): 1942-1949. In other words, these 1 million drivers are at risk for having a dangerous hypoglycemic event while operating a motor vehicle and not even realizing that they are having a hypoglycemic event before the symptoms impair their ability to safely operate the motor vehicle. This puts these diabetics, as well as other motor vehicle operators and bystanders, at an unnecessary and preventable risk.

Further, hypoglycemic events are positively correlated with insulin therapy. Indeed, an increased rate of hypoglycemic unawareness is found in diabetics using insulin therapy. See J. Diabetes Science and Technology, 2010: 4(2): 464-469. It is estimated that approximately 5.7 million American diabetics utilize insulin therapy. See Centers for Disease Control and Prevention. National diabetes fact sheet: national estimates and general information on diabetes and prediabetes in the United States, 2011. Atlanta, Ga.: U.S. Department of Health and Human Services, Centers for Disease Control and Prevention, 2011, which is herein incorporated by reference in its entirety. In short, many diabetic drivers are at risk for having a hypoglycemic event with no advance warning prior to physiological impairment, thus increasing their odds for having a motor vehicle accident. This risk is further increased with the addition of insulin therapy.

This long-standing problem has not gone unnoticed. Many states and some countries have implemented more stringent driving regulations and restrictions for diabetics and particularly for diabetics that are certain driver types (i.e., commercial truck drivers). However, these regulations and restrictions fall short from completely addressing the increased risk of motor vehicle accidents and incidences attributed to diabetes. Importantly, these restrictions and regulations are often in conflict with Federal and state laws and regulations, such as the Americans with Disabilities Act, which are concerned with preserving individual rights and protecting against discrimination. Thus, implementation of driving regulations and restrictions is an impractical solution to the long-standing problem at hand. Moreover, with advancements in diabetic therapy technologies and increased use of insulin therapies among diabetics, historical studies seriously underestimate and do not account for an exponentially increasing incidence of severe hypoglycemia. Suffice it to say, there exists a serious long-felt and unmet need for improving safety of motor vehicle operation by diabetics.

The embodiments disclosed herein seek to provide increased safety for diabetic drivers, while not infringing on individual rights, by providing a device which prevents or limits operation of a motor vehicle if a blood glucose concentration is outside of a predetermined blood glucose concentration range and if a blood glucose concentration measurement time is outside of a predetermined time range. In one embodiment, a vehicle controller determines if a blood glucose concentration, which is received from a glucometer, is within a predetermined blood glucose concentration range and determines if the received blood glucose concentration was measured within a predetermined time range. Upon determining that the blood glucose concentration is outside the predetermined blood glucose concentration range or that the received blood glucose concentration was measured outside the predetermined time range, the vehicle controller signals a gearshift relay interlock of a motor vehicle to inhibit gear shifting, thus preventing motor vehicle operation. With these concepts in mind, reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents.

With this in mind, attention is first directed to FIG. 1, which shows one embodiment of an in-vehicle blood glucose monitoring apparatus and motor vehicle operation control system. In one embodiment, a vehicle controller 101 having a receiver 107 and a transmitter 108 receives data, including but not limited to a blood glucose concentration and a blood glucose concentration measurement time, via the receiver 107 from a glucometer 102. In some embodiments, the vehicle controller 101 has an outer casing 109 that is separate and distinct from a motorized vehicle, which contains components of the vehicle controller, such as the receiver 107 and the transmitter 108. Preferably, the blood glucose concentration is the most recent blood glucose concentration measured by the operator. In the preferred embodiment, the blood glucose concentration measurement time comprises a time and a date when a blood glucose concentration was measured by the glucometer 102. Most preferably, the blood glucose concentration measurement time is the time and the date of a most recent blood glucose concentration measurement. The glucometer 102 is any blood glucose concentration-measuring device, including, but not limited to, a static measurement glucometer and a continuous measurement glucometer.

After receiving the data from the glucometer 102, the vehicle controller 101 determines if the blood glucose concentration is within a predetermined blood glucose concentration range and if the blood glucose concentration measurement time is within a predetermined time range. Preferably, the vehicle controller 101 validates the blood glucose concentration measurement and blood glucose concentration measurement time by reading the received blood glucose concentration measurement and blood glucose concentration measurement time twice. The predetermined blood glucose concentration range is discussed in greater detail with reference to FIG. 6. Upon determination, the vehicle controller 101 transmits, via the transmitter 108, a signal to control a state of a gearshift interlock relay 103 of a motor vehicle. Operation of the vehicle controller 101 is discussed in further detail in relation to FIG. 5. Preferably, the vehicle controller 101 can transmit the signal directly to the gearshift interlock relay 103. In other embodiments, the vehicle controller 101 transmits the signal to a third party, such as a telematic motor vehicle service, including, but not limited to OnStar® service, which then transmits a corresponding signal to control the state of the gearshift interlock relay 103 to the gearshift interlock relay 103. In further embodiments, a remote third party can initiate and independently transmit a signal to the vehicle controller 101 to control the state of the gearshift interlock relay 103. Stated differently, the remote third party can override the system, thus allowing the remote third party to control the state of the gearshift interlock relay 103 regardless of the results of a blood glucose concentration evaluation conducted by the operator.

The gearshift interlock relay 103 operates to control a gearshift solenoid 105, which, in combination with the gearshift interlock relay 103, controls locking and unlocking of a gear shifter in a motor vehicle. One having ordinary skill in the art will appreciate that the gearshift interlock relay 103 exists in either an energized state or a de-energized state. In most motor vehicles, when the gearshift interlock relay 103 is in a de-energized state, the gearshift solenoid 105 is disabled and the gearshift is locked. Thus, for example, if the vehicle controller 101 determines that the blood glucose concentration and blood glucose concentration measurement time are outside of their respective predetermined ranges, the vehicle controller 101 transmits a signal to de-energize the gearshift interlock relay 103.

Alternatively, in most motor vehicles, when the gearshift interlock relay 103 is in an energized state, the gearshift solenoid 105 is enabled, and the gearshift is unlocked. Thus, for example, if the vehicle controller 101 determines that the blood glucose concentration and the blood glucose concentration measurement time are within their respective predetermined ranges, the vehicle controller 101 transmits a signal to energize the gearshift interlock relay 103. One having ordinary skill in the art will appreciate that different configurations of the state of the gearshift interlock relay 103 may exist to lock and unlock the gearshift and are within the spirit and scope of this disclosure.

The vehicle controller 101 comprises any device or processing logic, including but not limited to, hardware and/or software capable of at least processing data and information received from a glucometer 102 and transmitting a signal to other devices or systems, including but not limited to, a mechanical or an electrical drive interlock referred to herein as a gearshift interlock relay 103. With this in mind, attention is directed to FIG. 2, which shows one embodiment of the in-vehicle blood glucose-monitoring apparatus and motor vehicle operation control system in which the vehicle controller (FIG. 1, 101) comprises a microprocessor 201. In one embodiment, the microprocessor 201 is contained within the outer casing (e.g. FIG. 1, 109) of the vehicle controller. For some embodiments, the microprocessor 201 comprises a computer-readable medium and is configured to receive and process any data or information, including but not limited to, a blood glucose concentration and a blood glucose concentration measurement time from a glucometer 102. In some embodiments, the glucometer 102 transmits data or information to the microprocessor 201 via connection wire, cable, universal serial bus (USB), or other suitable physical connection. In other embodiments, the glucometer 102 transmits data or information to the microprocessor 201 using a wireless signal such as radio frequency RF, Bluetooth® protocol, or other suitable wireless signal.

In operation, the microprocessor 201 determines if the blood glucose concentration is within a predetermined blood glucose concentration range, and also determines if the blood glucose concentration measurement time is within a predetermined time range. Upon determination, the microprocessor 201 transmits a signal to control the state of the gearshift interlock relay 103. This process is discussed in greater detail in relation to FIG. 5.

In some embodiments, the microprocessor 201 transmits the signal to control the gearshift interlock relay 103 directly to the gearshift interlock relay 103. Signal transmission can occur in some embodiments by transmission through a connection wire, cable, USB, or other suitable physical connection. Alternatively, signal transmission can occur wirelessly via RF, Bluetooth® protocol, or other suitable wireless signal. In further embodiments, the microprocessor 201 transmits the signal to control the gearshift interlock relay 103 wirelessly to a third party. For some embodiments, the third party is a telematic motor vehicle service, such as On Star® service or other similar service. The third party then transmits a corresponding signal to control the state of the gearshift interlock relay 103 to the gearshift interlock relay 103 of the motor vehicle.

Figure 2:
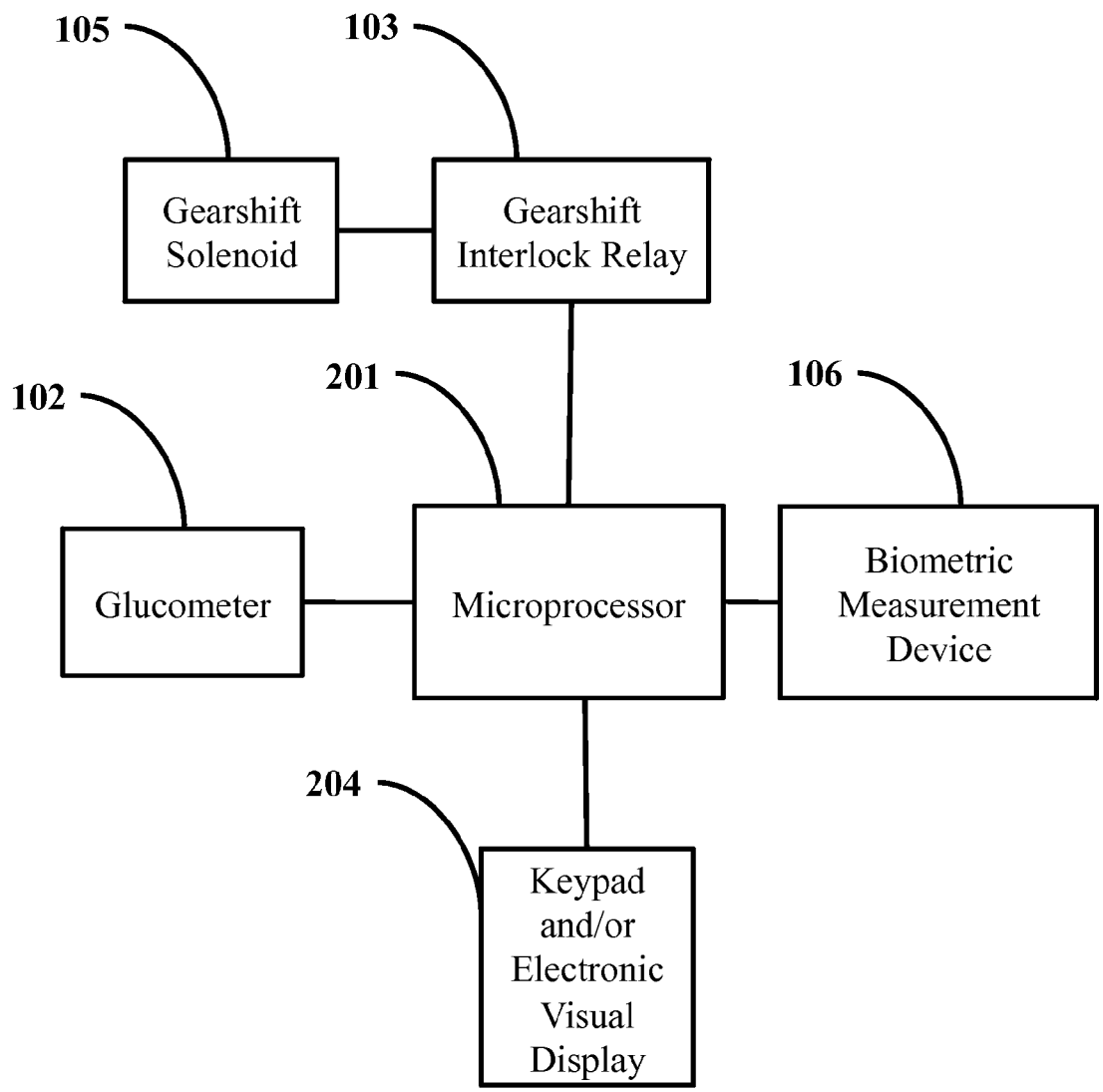
FIG. 2 shows one embodiment of an in-vehicle blood glucose-monitoring apparatus and motor vehicle operation control system in which a vehicle controller comprises a microprocessor.

Continuing with FIG. 1, in some embodiments, the vehicle controller 101 is integrated with or coupled to an operator interface 104. The operator interface 104 allows an operator to interact with, provide additional input data to, and otherwise control the vehicle controller 101. In some embodiments where the vehicle controller 101 is integrated with an operator interface 104, the operator interface 104 can be integrated with an outer casing 109, such that the user can directly interact with the vehicle controller. As shown in FIG. 2, in which the vehicle controller 101 comprises a microprocessor 201, for some embodiments, the operator interface (FIG. 1, 104) comprises a keypad 204. The keypad 204 allows the operator to input alphanumerical based data into the microprocessor 201. In some embodiments, the keypad 204 also includes simple buttons that allow direct execution of simple functions such as, but not limited to, "Yes," "No," "Enter," and "Delete."

In further embodiments, the operator interface (FIG. 1, 104) comprises an electronic visual display 204. The electronic vehicle display 204 visually displays system status information such as time, date, glucometer data and information, user identification information, time remaining until next blood glucose concentration measurement, a blood glucose concentration warning alarm, a time remaining until next blood glucose concentration warning alarm, and vehicle controller determination results. Preferably, the electronic visual display 204 is a liquid crystal display (LCD). In other embodiments the electronic visual display 204 is a light emitting diode (LED) display, organic LED (OLED) display, an active matrix OLED display, a graphical LCD (GLCD), a thin film transistor LCD (TFTLCD), a super TFT LCD, a 7-segment LCD, an in-plane switching LCD (IPSLCD), LED backlit IPS TFT LCD display, a holographic display, a 3-dimensional display, a plasma display, or a combination thereof. Preferably, the electronic visual display 204 comprises a touch screen display. Thus, preferably, the operator interacts with the electronic vehicle display 204 by simply touching the electronic visual display 204. In other embodiments, the operator interacts with the electronic vehicle display 204 through a keypad and/or simple buttons that allow direct execution of simple functions such as, but not limited to "Yes," "No," "Enter," and "Delete."

In some embodiments, the electronic visual display and/or the keypad 204 has indicator LEDs for indicating the status of the system. For example, the indicator LEDs can be colored or placed at specific locations on the electronic visual display and/or the keypad 204 to indicate system status such as a low blood glucose concentration, a high blood glucose concentration, an acceptable blood glucose concentration and an acceptable blood glucose concentration measurement time, a time until next blood glucose concentration measurement is required, and/or that re-measurement of blood glucose concentration is required. In other words, the LEDs indicate, based on a blood glucose concentration measurement and a blood glucose concentration measurement time, that an operator is permitted to operate the motor vehicle and a long timer is activated, which functions to remind the operator to re-measure their blood glucose concentration (blood glucose concentration is within a predetermined acceptable blood glucose concentration range and blood glucose concentration measurement time is within the predetermined time range), not permitted to operate the motor vehicle (blood glucose concentration is not within the predetermined blood glucose concentration range or blood glucose concentration measurement time is outside of a predetermined range), or that the operator is permitted to operate the motor vehicle and that a short timer is activated, which functions to remind the operator to re-measure their blood glucose concentration (blood glucose concentration is within a critical low or a critical high predetermined blood glucose concentration range and blood glucose concentration measurement time is within the predetermined time range).

Preferably, if the operator is permitted to operate the motor vehicle, a green LED indicates that the operator is safe to operate the motor vehicle and that a long timer has been activated which, upon expiration, will trigger an alarm to remind the operator to re-measure their blood glucose concentration. If the operator is not permitted to operate the motor vehicle, a red LED indicates that the operator has failed a blood glucose concentration evaluation. If the operator is permitted to operate the motor vehicle, but will need to re-measure their blood glucose concentration shortly thereafter, a yellow LED indicates a warning to the operator that a timer has been activated, which, upon expiration, will trigger an alarm to remind the operator to re-measure their blood glucose concentration. In other embodiments, the electronic visual display and/or the keypad 204 comprises an audible alarm that is activated by the microprocessor 201. The long timer and the short timer are discussed in further detail with reference to FIG. 5.

Many of the motor vehicles available today have an original equipment manufacture (OEM) onboard motor vehicle operator interface. Additionally, some operators install after market onboard motor vehicle operator interfaces to upgrade older motor vehicles or to simply enhance newer motor vehicles. The onboard motor vehicle operator interface, either OEM or aftermarket, typically comprise a visual display that usually located in a dashboard. The onboard motor vehicle operator interface provides system information, such as climate control system information, stereo system information, and navigation system information, to the operator and allows the operator to control these various motor vehicle systems. Examples of OEM onboard motor vehicle operator interfaces include, but are not limited to, MINI's Connected® system and Cadillac's Cue® system. Typical aftermarket onboard motor vehicle operator interfaces include, but are not limited to, car personal computers and advanced gaming systems, such as Playstation® system and Xbox® system. In addition to comprising many features, such as an electronic visual display, a keypad (virtual or physical), and indicator lights, the onboard motor vehicle user interface is configured to interact with various microprocessor systems in the motor vehicle.

The embodiments disclosed in relation to FIG. 2 are operated independent of an OEM onboard motor vehicle operator interface or an after market onboard motor vehicle operator interface. With this in mind attention is directed to FIG. 3, which shows one embodiment of an in-vehicle glucose monitoring apparatus and motor vehicle control system in which an operator interface (FIG. 1, 104) comprises an onboard motor vehicle operator interface 301. In a preferred embodiment, a glucometer 102 transmits data comprising a blood glucose concentration and a blood glucose concentration measurement time, to a microprocessor 201. The onboard motor vehicle operator interface 301 functions similarly to the electronic visual display (FIG. 2, 204). Stated differently, the operator controls and interacts with the microprocessor 201 through the onboard motor vehicle operator interface 301. Thus, for these embodiments, the onboard motor vehicle operator interface 301 is configured to display various in-vehicle glucose monitoring apparatus and vehicle control system status indicators, such as time, date, glucometer data and information, user identification information, time remaining until next blood glucose concentration measurement, and microprocessor 201 determination results.

In some embodiments the microprocessor 201 is independent from the onboard motor vehicle operator interface 301. In other embodiments, the microprocessor 201 is integrated with the onboard motor vehicle operator interface 301. The microprocessor 201 determines if the blood glucose concentration is within a predetermined blood glucose concentration range, and also determines if the blood glucose measurement time is within a predetermined time range. Upon determination, the microprocessor 201 transmits a signal to control a state of a gearshift interlock relay 103 of a motor vehicle. Operation of the microprocessor is described in greater detail in relation to FIG. 5.

Figure 3:
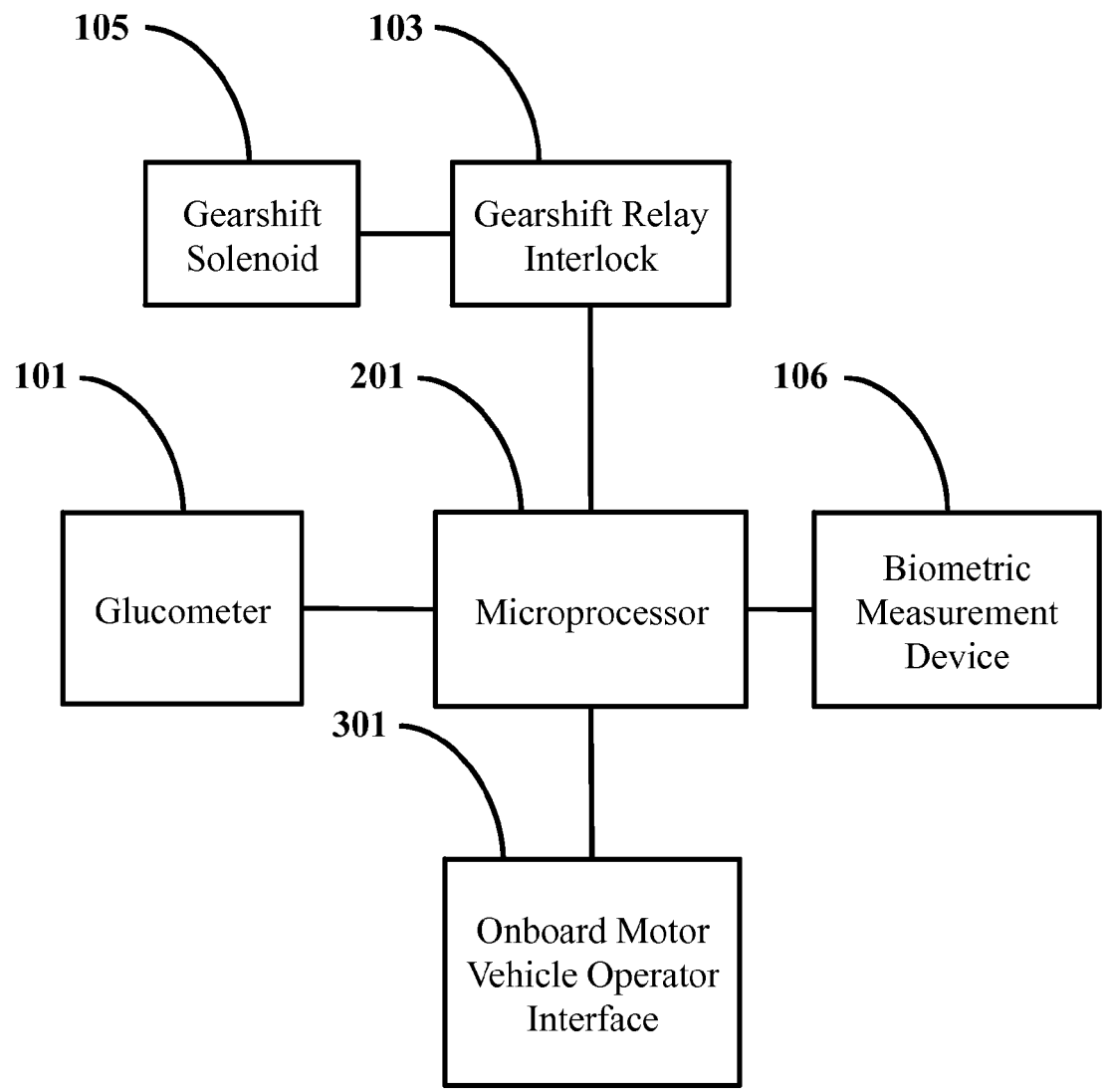
FIG. 3 shows one embodiment of an in-vehicle blood glucose-monitoring apparatus and motor vehicle operation control system in which an operator interface comprises an onboard motor vehicle operator interface.

As shown and described in relation to FIGS. 2 and 3, the vehicle controller (FIG.1, 101) comprises a microprocessor 201, which receives and processes data from a glucometer 102. Mobile devices, such as tablet personal computers and smart phones, are ubiquitous, are easy to use, and have functions that are highly adaptable by way of mobile applications and other similar software. With this in mind, attention is directed to FIG. 4, which shows one embodiment of the in-vehicle blood glucose-monitoring apparatus and motor vehicle operation control system in which the vehicle controller (FIG. 1, 101) is a mobile application 401, which is executed by a mobile device 402. For some embodiments the mobile application 401 is an Internet application that is executed by the mobile device 402. In other embodiments, the mobile application 401 is a software program executed by the mobile device 402 separate from the Internet. Preferably, the mobile device 402 is a mobile phone. In other embodiments the mobile device 402 is a laptop computer, tablet computer, personal digital assistant, or other suitable portable electronic device.

The mobile device 402 receives data and information, comprising a blood glucose concentration and a blood glucose concentration measurement time, from a glucometer 102. The mobile application 401 processes the data that is received by the mobile device 402 and determines if the blood glucose concentration is within a predetermined blood glucose concentration range. The mobile application 401 also determines if the blood glucose concentration measurement time is within a predetermined time range. Upon determination, the mobile application 401 directs the mobile device 402 to transmit a signal to control the state of the gearshift interlock relay 103 of the motor vehicle. This process is discussed in greater detail in relation to FIG. 5.

For these embodiments, the operator interface (FIG. 1 104) is a mobile device 402. Thus, for the embodiments described in relation to FIG. 4, the operator interacts with the mobile application 401 by using preexisting features of the mobile device 402. These preexisting features typically include, but are not limited to a display screen, a keypad (virtual or physical), a speaker, internet access, a visual indicator light, text messaging, e-mail capability, phone service, an internal clock, and a timer. The mobile application 401 is configured in the several embodiments to utilize the preexisting features of the mobile device 402. For example, the mobile application 401 can direct the mobile device 402 to provide a visual notification, such as a message on the display screen or flash an indicator light, to indicate system status, such as, but not limited to, a high blood glucose concentration, a low blood glucose concentration, mobile application blood glucose concentration determination results, time remaining until blood glucose concentration measurement is required, time since last blood glucose concentration measurement, and/or that measurement of blood glucose concentration is required. In further embodiments, the mobile application 401 can direct the mobile device 402 to sound an alarm such as a ring tone or vibration to provide a notification to the operator. One having ordinary skill in the art will appreciate that different ring tones can be used to differentiate between different system statuses.

Suffice it to say, the notification (visual or audio) indicates, based on a blood glucose concentration measurement and a blood glucose concentration measurement time, that an operator is permitted to operate the motor vehicle (blood glucose concentration and blood glucose concentration measurement time are within their respective predetermined ranges), not permitted to operate the motor vehicle (blood glucose concentration is outside the predetermined blood glucose concentration range or blood glucose measurement time is outside of a predetermined range), or that the operator is permitted to operate the motor vehicle, but should re-measure blood glucose concentration shortly (blood glucose concentration is within a critical low or a critical high predetermined blood glucose concentration range). The short timer and the long timer are described in greater detail with reference to FIG. 5. In short, the notification (visual or audio) indicates to an operator that they are permitted to operate the motor vehicle when their blood glucose concentration and blood glucose concentration measurement time is within their respective predetermined ranges, they are not permitted to operate the motor vehicle when they have failed the blood glucose concentration evaluation, and warn the operator that they are required to re-measure their blood glucose concentration.

In other embodiments, the mobile application 401 can direct the mobile device 402 to send a text message, an automatic outbound phone call, or an e-mail from the mobile device 402 to a third party to notify the third party of the status of the system. The third party can be a telematic motor vehicle service, such as On Star® service, or any other person. One can easily appreciate that this is particularly advantageous in an event where hypo- or hyper glycemia results in unconsciousness of the operator. Notification of a third party of the system status is also advantageous where remote monitoring of the operator is important. For example, third party monitoring of operators may be important to ensure the safety of operators at an increased risk for driving mishaps or need to comply with state and Federal regulations. In further embodiments, a remote third party can initiate and independently transmit a signal to the mobile application 401 or mobile device 402 to control the state of the gearshift interlock relay 103. Stated differently, the remote third party can override the system, thus allowing the remote third party to control the state of the gearshift interlock relay 103 regardless of the results of a blood glucose concentration evaluation conducted by the operator.

For some embodiments, the glucometer 102 transmits data or information to the mobile device 402 via a connection wire, cable, universal serial bus (USB), or other suitable physical connection. In other embodiments, the glucometer 102 transmits data or information to the mobile device 402 using a wireless signal such as radio frequency (RF), Bluetooth® protocol, or other suitable wireless signal. In some embodiments, the mobile device 402 transmits the signal to control the gearshift interlock relay 103 directly to the gearshift interlock relay 103. Signal transmission can occur in some embodiments via transmission through a connection wire, cable, USB, or other suitable physical connection. Alternatively, signal transmission can occur wirelessly via RF, Bluetooth® protocol, or other suitable wireless signal.

In further embodiments, the mobile application 401 transmits the signal to control the gearshift interlock relay 103 wirelessly to a third party. For some embodiments, the third party is a telematic motor vehicle service such as On Star® service or other similar service. The third party then transmits a corresponding signal to control the state of the gearshift interlock relay 103 to the gearshift interlock relay 103 of the motor vehicle.

Figure 4:
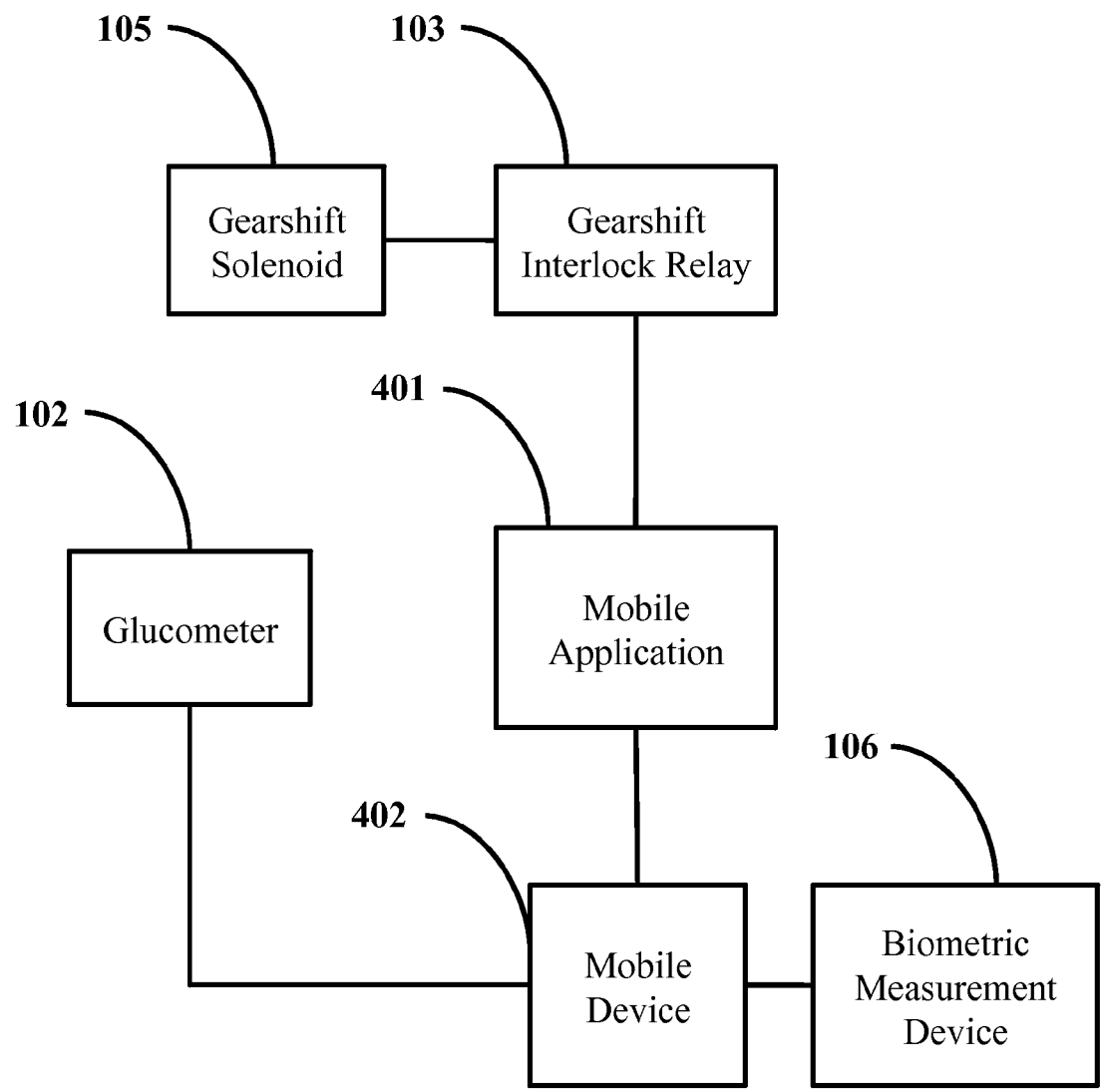
FIG. 4 shows one embodiment of an in-vehicle blood glucose-monitoring apparatus and motor vehicle operation control system in which a vehicle controller comprises a mobile application that is executed by a mobile device.

Insofar as a motor vehicle may have multiple operators, one advantage of the disclosed embodiments is that they provide various mechanisms for operator identification. Continuing with FIG. 1, preferably, operator identification data is transmitted to the vehicle controller 101 through the operator interface 104. For example, in some embodiments, operator identification is communicated to the microprocessor (FIG. 2, 201) via inputting a unique number, word, or combination thereof through the keypad and/or visual display (FIG. 2, 204). In other embodiments, operator identification is communicated to the microprocessor (FIG. 3, 201) via inputting a unique number, word, or combination thereof through the keypad and/or visual display that is part of the onboard motor vehicle control interface (FIG. 3, 301). In yet further embodiments, operator identification is communicated to the mobile application (FIG. 4, 401) via inputting a unique number, word, or combination thereof through the keypad and/or visual display that is part of the mobile device (FIG. 4, 402). In some embodiments the mobile phone application (FIG.4, 401) automatically reads a identification number of a mobile phone (FIG. 2, 402) and uses the mobile phone identification number to identify the operator.

Although an alphanumeric operator identification is a convenient and simple way to provide operator identification, some instances warrant use of a biometric characteristic to identify operators. Thus, for some embodiments, the vehicle controller 101 is configured to receive and process biometric data, including, but not limited to, breath data, fingerprint and retinal scans, and/or voice. The biometric data is collected by a biometric measurement device 106, which is, for example, a fingerprint scanner, a retinal scanner, a breathalyzer, or a voice recognition device. For some embodiments, the biometric measurement device 106 transmits the biometric data to the vehicle controller 101. For example, in some embodiments the biometric measurement device 106 transmits the biometric data to a microprocessor (FIG. 2, 201 and FIG. 3, 201). In other embodiments, the biometric measurement device 106 transmits the biometric data to a mobile device (FIG.4. 402).

A blood glucose concentration measurement would not be an appropriate biometric characteristic because it cannot be used to uniquely identify an individual. For example, while two operators my have unique finger prints from one another, it is very possible that they could both measure their blood glucose concentration and have the exact same blood glucose concentration as one another. Thus, their blood glucose concentration could not be used to tell them apart from one another.

Figure 5:
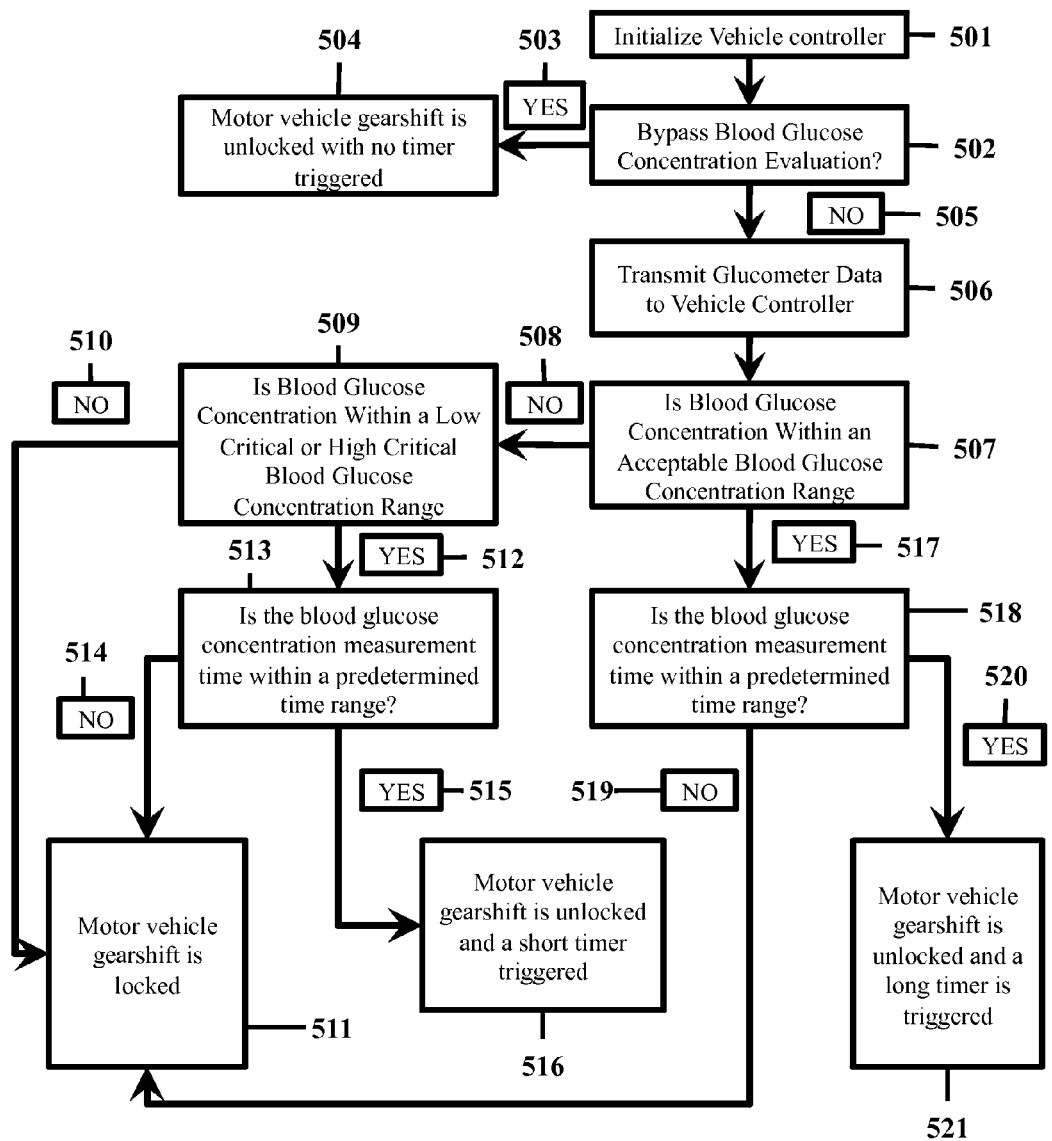
FIG. 5 shows one embodiment of a method to control motor vehicle operation in response to a blood glucose concentration and a blood glucose concentration measurement time.

With an understanding of the several embodiments described in relation to FIGS. 1-4 in mind, attention is now directed to FIG. 5, which shows one embodiment of a process to control motor vehicle operation in response to a blood glucose concentration and a blood glucose concentration measurement time. For sake of clarity, the process shown in FIG. 5 will be described in relation to the components as described in FIG. 1. However, it will be appreciated that the same steps in the process of operation apply to embodiments that employ a microprocessor (FIG. 2, 201 and FIG. 3, 201), or a mobile application (FIG. 4, 401).

In a preferred embodiment, operation of the in-vehicle blood glucose-monitoring apparatus and motor vehicle operation control system begins by initializing 501 the vehicle controller 101. For some embodiments, during initialization 501 the operator defines the predetermined blood glucose concentration range. In other embodiments, the predetermined blood glucose concentration range is pre-programmed with default values, thus requiring no operator input to define the predetermined blood glucose concentration range. Preferably, the predetermined glucose concentration range comprises an acceptable blood glucose concentration range, a high critical predetermined blood glucose concentration range, and a low critical predetermined blood glucose concentration range.

Figure 6:
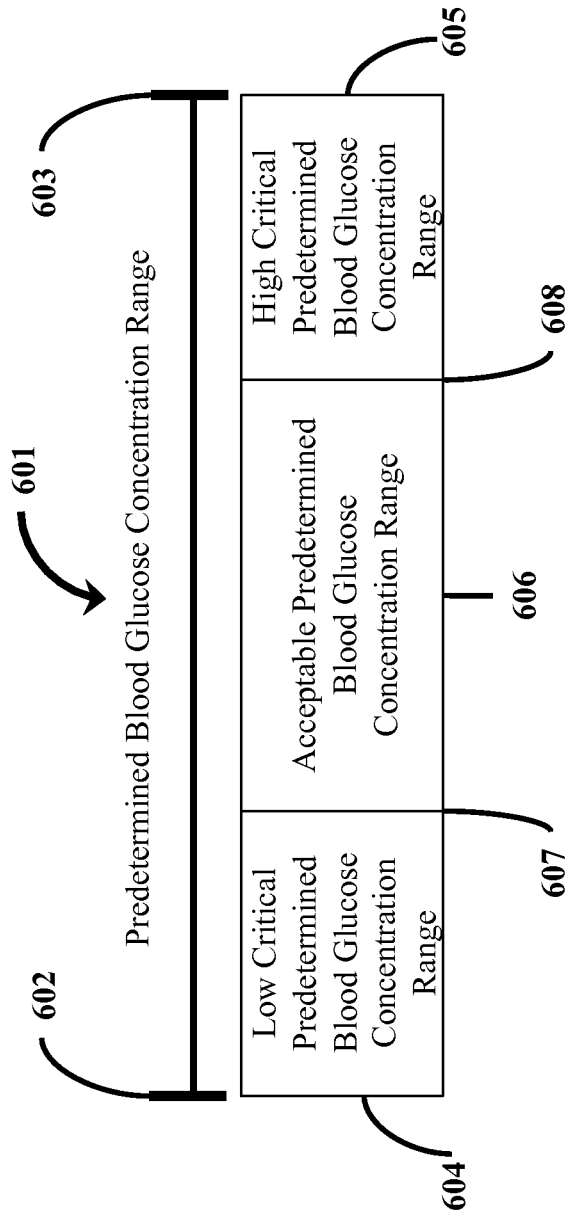
FIG. 6 shows one embodiment of a predetermined blood glucose concentration range.

To fully appreciate the several embodiments of the predetermined blood glucose concentration range, attention is directed to FIG. 6, which shows a one embodiment of the predetermined blood glucose concentration range 601. As shown in FIG. 6, in one embodiment the predetermined blood glucose concentration range 601 corresponds to blood glucose concentration values between a minimum blood glucose concentration value 602 and a maximum blood glucose concentration value 603. In the preferred embodiment, the predetermined blood glucose concentration range 601 comprises a low critical predetermined blood glucose concentration range 604, a high critical predetermined blood glucose concentration range 605, and an acceptable predetermined blood glucose concentration range 606. In the preferred embodiment, the low critical predetermined blood glucose concentration range 604 corresponds to blood glucose concentration values ranging from the minimum blood glucose concentration value 602 to a lower-limit blood glucose concentration value 607 of the acceptable predetermined blood glucose concentration range 606. The high critical predetermined blood glucose concentration range 605 corresponds to blood glucose concentration values ranging from the maximum blood glucose concentration value 603 to an upper-limit blood glucose concentration value 608 of the acceptable predetermined blood glucose concentration range 606.

In one embodiment, the vehicle controller 101 is pre-programmed with default values for the minimum blood glucose concentration value 602, maximum blood glucose concentration value 603, and lower-limit 607 and upper-limit 608 blood glucose concentration values of the acceptable predetermined blood glucose concentration range 606. The default maximum blood glucose concentration value is preferably 350 miligrams per deciliter (mg/dL), but can be any blood glucose concentration value in the range of aproximately 100 mg/dL to approximately 500 mg/dL. The default minimum blood glucose concentration value is preferably 70 mg/dL, but can be any blood glucose concentration value in the range of approximately 60 mg/dL to approximately 200 mg/dL. The default lower-limit blood glucose concentration value of the acceptable predetermined blood glucose concentration range 606 is preferably 80 mg/dL, but can be any blood glucose concentration value in the range of approximately 60 mg/dL to 200 mg/dL. The default upper-limit blood glucose concentration value of the acceptable predetermined blood glucose concentration range 606 is preferably 250 mg/dL, but can be any value in the range of approximately 100 mg/dL to approximately 350 mg/dL.

For other embodiments, the operator sets the minimum blood glucose concentration value 602 and the maximum blood glucose concentration value 603 during initialization (FIG. 5, 501). In other words, the operator defines the predetermined blood glucose range 601 by setting the minimum 602 and the maximum 603 blood glucose concentration values. The vehicle controller 101 determines the acceptable blood glucose concentration range 606 by calculating the lower-limit blood glucose concentration value 607 and the upper-limit blood glucose concentration value 608 of the acceptable blood glucose concentration range 606. Suffice it to say, the low critical predetermined blood glucose concentration range 604 corresponds to the blood glucose concentration values that lie between the minimum blood glucose concentration value 602 set by the operator and the lower-limit 607 of the acceptable predetermined blood glucose concentration range 606. Similarly, the high critical predetermined blood glucose concentration range 605 corresponds to the maximum blood glucose concentration value 603 set by the operator and the upper-limit 608 of the acceptable predetermined blood glucose concentration range 606. An advantage of these embodiments is that the predetermined range is customizable to fit the needs of any operator.

In some embodiments, the vehicle controller 101 calculates the lower-limit 607 of the acceptable predetermined blood glucose concentration range 606 as a percent of the minimum blood glucose concentration value 602 set by the operator. Similarly, in these embodiments, the vehicle controller 101 calculates the upper-limit 608 of the acceptable predetermined blood glucose concentration range 606 as a percent of the maximum blood glucose concentration value 603 set by the operator. For some embodiments the percentage used to calculate the lower-limit 607 of the acceptable predetermined blood glucose concentration range 606 is less than the percentage used to calculate the upper-limit 608 of the acceptable predetermined blood glucose concentration range 606. In other embodiments, the percentage used to calculate the lower-limit 607 of the acceptable predetermined blood glucose concentration range 606 is greater than the percentage used to calculate the upper-limit 608 of the acceptable predetermined blood glucose concentration range 606. In yet further embodiments, the percentage used to calculate the upper-limit 608 of the acceptable predetermined blood glucose concentration range 606 that is substantially identical to the percentage used to calculate the upper-limit 608 of the acceptable predetermined blood glucose concentration range 606.

Preferably, the vehicle controller 101 calculates the lower-limit blood glucose concentration value 607 of the acceptable blood glucose concentration range 606 based on a percentage of the minimum blood glucose concentration value 602 set by the operator and a blood glucose concentration measurement time received. Similarly, in the preferred embodiment, the vehicle controller 101 calculates the upper-limit blood glucose concentration value 608 of the acceptable predetermined blood glucose concentration range 606 based on a percentage of the maximum blood glucose concentration value 603 set by the operator and the blood glucose concentration measurement time received. One having ordinary skill in the art will appreciate that the blood glucose concentration measurement time used to determine the lower-limit 607 and the upper-limit 608 blood glucose concentration values of the acceptable blood glucose concentration range 606 preferably corresponds to the blood glucose concentration measurement time associated with the blood glucose concentration value being currently evaluated. Suffice it to say, in the preferred embodiment, the acceptable predetermined blood glucose concentration range 606 is a function of the operator defined minimum and maximum blood glucose concentration values as well as how much time has elapsed since the operator measured their blood glucose concentration.

In further embodiments, the operator sets the minimum blood glucose concentration value 602, the maximum blood glucose concentration value 603, and the lower-limit 607 and the upper-limit 608 blood glucose concentration values of the acceptable predetermined blood glucose concentration range 606 during initialization (FIG. 5, 501). In these embodiments, the low critical predetermined blood glucose concentration range 604 corresponds to the blood glucose concentration values that lie between the minimum blood glucose concentration value 602 and the lower-limit value 607 of the acceptable blood glucose concentration range 606. Similarly, in these embodiments the high critical predetermined blood glucose concentration range 605 corresponds to the blood glucose concentration values that lie between the upper-limit value 608 of the acceptable blood glucose concentration range 606 and the maximum blood glucose concentration value 603. An advantage of these embodiments is that the predetermined range is completely customizable to fit the needs of any operator.

In some embodiments, the vehicle controller is pre-programmed with an absolute low and/or an absolute high blood glucose concentration value, so as to prevent the operator from setting a blood glucose concentration range that would negate the function of the system. In other words, the absolute low and/or the absolute high blood glucose concentration values are in addition to an operator set or a calculated predetermined blood glucose concentration range 601 to prevent an operator from overriding the system. In these embodiments, the vehicle controller 101 will not allow gear shifting if the vehicle controller 101 determines that the blood glucose concentration is beyond the absolute low blood glucose concentration value or beyond the absolute high blood glucose concentration value, irrespective of the blood glucose concentration measurement time. For example, if an absolute low blood glucose concentration value is set and the blood glucose concentration is determined to be less than the absolute low blood glucose concentration value, the vehicle controller 101 will signal the gearshift interlock relay 103 to lock the gearshift, thus preventing motor vehicle operation. Preferably, the absolute low blood glucose concentration value is 70 mg/dL, but can be any blood glucose concentration value in the range of approximately 60 mg/dL to approximately 200 mg/dL. Preferably, the absolute high blood glucose concentration value is 350 mg/dL, but can be any blood glucose concentration value in the range of approximately 100 to 500 mg/dL.

Another aspect of the disclosed embodiments is that the vehicle controller 101 validates any operator defined predetermined blood glucose concentration range. In other words, in some embodiments the vehicle controller 101 determines if the operator defined predetermined blood glucose concentration ranges make functional and logical sense. For example, the vehicle controller 101 determines if an operator set minimum blood glucose concentration value is, in fact, less than an operator set maximum blood glucose concentration value. As another non-limiting example, the vehicle controller 101 determines if a predetermined blood glucose concentration range resulting from operator entered blood glucose concentration values, such as a minimum 602 and a maximum 603 blood glucose concentration value, creates a predetermined usable blood glucose concentration range. One having ordinary skill will appreciate that if there are no blood glucose concentration values separating the minimum 602 and the maximum 603 blood glucose concentration values, then there is not a functional predetermined blood glucose concentration range. If the vehicle controller 101 determines that the operator defined predetermined ranges are not logical or would not produce a functional blood glucose concentration range, for example, then the operator defined blood glucose concentration values are not accepted by the vehicle controller 101 and the operator will have to set new blood glucose concentration values.

With an understanding of the predetermined blood glucose concentration range and absolute blood glucose concentration values in mind, discussion of the operation of the in-vehicle blood glucose-monitoring apparatus and motor vehicle operation control system continues with further discussion of FIG. 5. The operator can manually set other parameters during initialization 501 besides predetermined blood glucose concentration range information. For example, the operator can set operator individual identification codes or biometric characteristic baselines, such as fingerprints and the like, that will be used as operator identification. The operator sets these parameters by interacting with the operator interface 104. Additionally, the operator can input glucometer serial codes, which will allow the vehicle controller 101 to recognize and communicate with the glucometer 102, such as via a Bluetooth® protocol.

Moreover, the operator can program the vehicle controller 101 to correlate operator identification information or operator biometric characteristics with a specific acceptable blood glucose concentration range or ranges. In other words, the vehicle controller can be programmed to have distinct operator profiles. Thus, each operator will have an operator profile comprising information unique to that operator, such as a glucometer serial number, biometric baselines, operator identification codes, predetermined blood glucose concentration ranges, minimum and maximum blood glucose concentration values (FIG. 6, 602 and 603, respectively), lower-limit and upper-limit blood glucose concentration values (FIG. 6, 607 and 608, respectively) for the acceptable predetermined blood glucose concentration range (FIG. 6, 606), and absolute low and absolute high blood glucose concentration values. This is advantageous for motor vehicles operated by multiple operators, particularly for motor vehicles operated by multiple diabetic operators, as it allows the system to easily recognize the operator and apply their predetermined blood glucose concentration range or default predetermined blood glucose concentration range. It will be appreciated that initialization 501 can be repeated as many times as necessary, as blood glucose concentration management may change over time. It will also be appreciated that, other than prior to a first use of the system, initialization 501 is an optional step. Thus, in some embodiments, use of the system begins with the operator determining if they want to bypass blood glucose concentration evaluation 502.

In operation, when the operator enters in, for example, their operator identification number, the vehicle controller 101 will recognize that the operator is permitted to bypass blood glucose concentration evaluation and transmits a signal to unlock the gearshift. In other words, by inputting their operator identification information, the operator determines to 503 bypass or not 505 to by pass the blood glucose concentration evaluation process. The vehicle controller 101 is programmed during initialization 501 to recognize which operators, via their operator profile information, are permitted to bypass 503 blood glucose concentration evaluation and which operators are not 505 permitted to bypass blood glucose concentration evaluation.

With that said, after initialization 501, or when an operator wants to operate a motor vehicle without initializing the vehicle controller 501, an operator determines if they want to bypass blood glucose concentration evaluation 502. This aspect of the disclosed embodiments is particularly advantageous for when the disclosed device and system is used in a motor vehicle that is operated by both diabetics and non-diabetics, as non-diabetics do not have a need to monitor their glucose concentration. If it is determined 503 that blood glucose concentration evaluation is to be bypassed, then the vehicle controller 101 transmits a signal to the gearshift interlock relay 103, which unlocks the motor vehicle gearshift without triggering a timer 504. The timer, which is not triggered if blood glucose evaluation is bypassed 503, is designed to remind diabetics to re-measure their blood glucose concentration and is discussed in greater detail relation to other steps in the process.

In contrast, if the operator determines not 505 to bypass blood glucose concentration evaluation 502, then data is transmitted to the vehicle controller 506 from the glucometer. The transmitted data comprises information including, but not limited to, a blood glucose concentration and a blood glucose concentration measurement time. Preferably, the blood glucose concentration measurement time is the date and the time of the most recent blood glucose concentration measurement and the blood glucose concentration is the most recent blood glucose concentration measured by the operator.

Upon receiving data from the glucometer 102, the vehicle controller 101 determines if the blood glucose concentration is within the acceptable blood glucose concentration range 507. Preferably, the blood glucose concentration is the most recent blood glucose concentration measured by the operator. If the vehicle controller 101 determines that the blood glucose concentration is not 508 within the acceptable blood glucose concentration range, then the vehicle controller 101 determines if the blood glucose concentration is within a low critical or a high critical blood glucose concentration range 509. If the vehicle controller 101 determines that the blood glucose concentration is not 510 within a low critical or a high critical blood glucose concentration range, the vehicle controller transmits a signal so that the motor vehicle gearshift is locked 511, and motor vehicle operation is inhibited.

However, if the vehicle controller 101 determines 512 that the blood glucose concentration is within a low critical or a high critical blood glucose concentration range, then the vehicle controller determines if the blood glucose concentration measurement time is within a predetermined time range 513. Preferably, the blood glucose concentration is the most recent blood glucose concentration measured by the operator. To rearticulate, the blood glucose concentration measurement time is the time and the date when the operator measured their blood glucose concentration. Preferably, the blood glucose concentration measurement time is the date and the time of the most recent blood glucose concentration measurement. In some embodiments, the vehicle controller 101 comes pre-programmed with the predetermined time range. In other embodiments, the operator can set the predetermined time range during initialization 501.

If the vehicle controller 101 determines that the blood glucose concentration measurement time is not 514 within the predetermined time range, then the vehicle controller 101 transmits a signal to the gear shift interlock relay 103 to lock the motor vehicle gearshift 511, thus inhibiting motor vehicle operation. In contrast, if the vehicle controller determines that the blood glucose concentration measurement time is 515 within the predetermined time range, then the vehicle controller 101 triggers a short timer and transmits a signal to the gearshift interlock relay 103 to unlock the motor vehicle gearshift 516, thus allowing motor vehicle operation.

In contrast, if the vehicle controller 101 determines that the blood glucose concentration is 517 within the acceptable blood glucose concentration range, the vehicle controller 101 then determines if the blood glucose concentration measurement time is within a predetermined time range 518. If the vehicle controller 101 determines that the blood glucose concentration measurement time is not 519 within the predetermined time range, then the vehicle controller 101 transmits a signal to the gearshift interlock relay 103 to lock the gearshift 511. However, if the vehicle controller 101 determines that the blood glucose concentration measurement time is 520 within the predetermined time range, then the vehicle controller 101 triggers a long timer and transmits a signal to the gearshift interlock relay 103 to unlock the motor vehicle gearshift 516, thus allowing motor vehicle operation.

In some embodiments, the timer length is a function of which predetermined blood glucose concentration range (i.e., low critical, high critical, or acceptable) the blood glucose concentration measurement falls into. In other words, the timer length is independent of an exact blood glucose concentration measurement and blood glucose concentration measurement time. The short timer is set for anywhere between approximately zero (0) hours to approximately three (3) hours, but is preferably set for approximately fifteen (15) min-approximately one (1) hour. The long timer is set for any length of time longer than what the short timer is set for, but is preferably set for one (1) to four (4) hours.

In other embodiments, the short and the long timer are calculated based on an exact blood glucose concentration measurement and/or an exact blood glucose concentration measurement time. In these embodiments, timer length is related to how close the blood glucose concentration value is to a midpoint blood glucose concentration value of the acceptable predetermined blood glucose concentration range (FIG. 6, 606). Additionally, timer length is also inversely proportional, within a predetermined blood glucose concentration range (i.e., acceptable, low critical, or high critical), to how recent the last blood glucose concentration measurement was. In other words, given two blood glucose concentration values that are both found within the same predetermined blood glucose concentration range (i.e., low critical, high critical, or acceptable), a blood glucose concentration value that was measured one (1) minute prior to blood glucose concentration evaluation will have a longer timer than a blood glucose concentration value that was measured three (3) hours prior to blood glucose concentration evaluation. In short, for these embodiments the timers are calculated such that a blood glucose concentration measurement falling within the acceptable predetermined blood glucose concentration range (FIG. 6, 606) will never trigger a shorter timer than a blood glucose concentration measurement falling in the low critical (FIG. 6, 604) or high critical (FIG. 6, 605) blood glucose concentration ranges. Similarly, within a given predetermined blood glucose concentration range, a more recent blood glucose concentration measurement will never trigger a shorter timer than a less recent blood glucose concentration measurement.

As previously mentioned, the timer functions to remind an operator to re-measure their blood glucose concentration. When a timer has expired, an alarm occurs to signal to the operator that they need to re-measure their blood glucose concentration. The alarm is any audible or visual signal suitable to provide notification to the operator. For example, in some embodiments, the alarm can be a tone that is sounded repetitively, similar to a seat belt warning alarm. In other embodiments, the alarm can be a visual indicator such as an LED or word message displayed on the operator interface 104. For some embodiments the alarm can be a message, such as a text, phone, or email message, sent to a third party and/or the operator. If the operator ignores the alarm for a period of time, in some embodiments the alarm becomes increasingly more annoying to further encourage the operator to re-measure their blood glucose concentration. In short, the alarm acts as an annoyance to remind and encourage an operator to re-measure their blood glucose concentration.

For some embodiments the timer is short 516. In other embodiments, the timer is long 521. Yet in other embodiments, the timer is not triggered at all 504. The difference in timers is a reflection of an operator's physiological status. For example, if the operator is not diabetic, then there is no need to evaluate blood glucose concentration, and thus there is no need to re-measure blood glucose concentration. Therefore, a timer to remind the operator to re-measure blood glucose concentration is not necessary.

In contrast, if an operator is diabetic and the vehicle controller 101 determines that the blood glucose concentration is 512 within a low critical or a high critical blood glucose concentration range and that the blood glucose concentration measurement time is within a predetermined time range 515, the diabetic operator is not at a significant enough risk for experiencing hyperglycemic or hypoglycemic impairments so as to completely inhibit motor vehicle operation. However, since the blood glucose concentration is in a range (a high critical range or a low critical range) where the diabetic operator has an increased risk of experiencing hyperglycemic or hypoglycemic impairments, it is prudent that the diabetic operator re-measure their blood glucose concentration at a shorter time interval than if the blood glucose concentration is 517 within the acceptable blood glucose concentration range and the blood glucose concentration measurement time is 520 within the predetermined time range.

In contrast, if an operator is diabetic and the vehicle controller 101 determines that the blood glucose concentration is 517 within the acceptable blood glucose concentration range, but determines that the blood glucose concentration measurement time is not 519 within the predetermined time range, the diabetic may be at a risk for a hyper- or a hypoglycemic event significant enough to inhibit motor operation. Similarly, if an operator is diabetic and the vehicle controller 101 determines that the blood glucose concentration is not 508 within the acceptable blood glucose concentration range and is also not 510 within the low critical or high critical blood glucose concentration range, the diabetic is at great risk for experiencing, if not already experiencing, a hyper- or a hypoglycemic event. Thus, motor vehicle operation is accordingly inhibited. Insofar as the diabetic operator is at a significant risk for experiencing hyperglycemic or hypoglycemic impairments, or is already experiencing a hyper- or a hypoglycemic event, it is prudent that the motor vehicle gearshift is locked until the diabetic operator re-measures and re-evaluates their blood glucose concentration and the vehicle controller 101 determines, by the aforementioned process, to unlock the gearshift and allow motor vehicle operation.

In some embodiments, the long timer and the short timer are preprogrammed into the vehicle controller 101. In other embodiments, an operator manually sets the long timer and the short timer during initialization 501. In yet further embodiments, an absolute minimum and/or an absolute maximum length of time for the long timer and the short timer are preprogrammed, which still allows the operator to manually set the long timer and the short timer during initialization 501, but does not allow the operator to manually set the long timer and the short timer so as to negate the purpose of the timer.

The aspect of a timer is a key advantage of the disclosed embodiments. Insofar as it acts as a reminder to re-measure blood glucose concentration, rather than an inhibitor of motor vehicle operation, it allows the operator to utilize a motor vehicle when risk of impairment due to hyperglycemia or hypoglycemia is relatively low. Additionally, the aspect of a timer encourages regular blood glucose monitoring both during motor vehicle operation and during other times. Therefore, the disclosed embodiments can positively impact a diabetic's overall health, as well as improving safety of motor vehicle operation.

The timer is also advantageous during long periods of motor vehicle operation as blood glucose concentration can change, sometimes dramatically, over time. For example, the timer is particularly useful for diabetic commercial truckers, which must comply with regulations that require quarterly reporting of blood glucose concentration monitoring. For some embodiments, the vehicle controller 101 can be configured to store data, such as blood glucose concentration measurement time, blood glucose concentration, and blood glucose concentration evaluation results. In these embodiments, the commercial truck driver, for example, has easy access to this data to submit to the Department of Transportation for required quarterly assessments.

In sum, the aforementioned embodiments encompass a device and method that strikes a balance between freedom to operate a motor vehicle by diabetics, while improving motor vehicle operation safety by decreasing the risk that a diabetic will operate a motor vehicle when hypo- or hyperglycemic. In addition to the aforementioned advantages of the presently disclosed embodiments, the systems and methods disclosed herein also have the unique advantage over other systems by controlling motor vehicle operation by inhibiting only gear shifting in response to a blood glucose concentration value that is outside of a predetermined blood glucose concentration range or a blood glucose concentration measurement time that is outside of a predetermined time range. Stated differently, the present disclosure allows an operator to turn on a motor vehicle and control environmental comforts such as heat or air conditioning, but not shift the motor vehicle into gear in the event blood glucose concentration or blood glucose concentration measurement time is not within a desired concentration or time range, respectively. Thus, an operator can utilize important safety and comfort features, such as an air conditioner or heater, of the motorized vehicle but not drive it when at risk for, or experiencing, a hypo- or hyperglycemic state and treat their condition accordingly. This is a distinct advantage over other devices that inhibit motor vehicle operation by employing or engaging an ignition interlock.

Any process descriptions or blocks in flow charts should be understood as representing modules, segments, or portions of code which include one or more executable instructions for implementing specific logical functions or steps in the process, and alternate implementations are included within the scope of the preferred embodiment of the present disclosure in which functions may be executed out of order from that shown, or discussed, including substantially concurrently or in reverse order, depending on the functionality involved, as would be understood by those reasonably skilled in the art of the present disclosure.

For some embodiments the microprocessor may comprise a program that may be implemented in hardware, software, firmware, or a combination thereof. In the preferred embodiment(s), the program is implemented in microprocessor hardware using any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc. In an alternative embodiment, the program is implemented in software or firmware that is stored in a memory and that is executed by a suitable instruction execution system.

Similarly, while the mobile application is likely implemented as a software application, it should be appreciated that the functions of the mobile application can be implemented in hardware by using the above-recited hardware technologies. In other words, those having skill in the art will appreciate that the programmable components recited herein can be implemented in either hardware or software.

In the context of this document, a "computer-readable medium" can be any means that can contain, store, communicate, propagate, or transport data or information, or execute a software program for use by or in connection with the instruction execution system, apparatus, or device. The computer-readable medium can be, for example but not limited to, an electronic, magnetic, optical, electromagnetic infrared, or semiconductor system, apparatus device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), a Secured Digital (SD) Card (electronic), an optical fiber (optical), and a portable compact disc read-only memory (CDROM) (optical). Note that the computer-readable medium could even be paper or another suitable medium upon which the program is printed, as the program can be electronically captured via, for instance, optical scanning of the paper or other medium, then compiled, interpreted or otherwise processed in a suitable manner if necessary, and stored in a computer memory.

Although exemplary embodiments have been shown and described, it will be apparent to those of ordinary skill in the art that a number of changes, modifications, or alterations to the disclosure as described may be made. All such changes, modifications, and alterations should therefore be seen as within the scope of the disclosure.

What is claimed is:

1. A motorized vehicle control apparatus comprising:
an outer casing;
a receiver to receive a blood glucose concentration measurement and a blood glucose concentration measurement time and date from a glucometer, wherein the receiver is contained within the outer casing;
a microprocessor to compare the blood glucose concentration measurement to a predetermined blood glucose concentration range, the microprocessor to further compare the blood glucose concentration measurement time and date to a predetermined time and date range, wherein the microprocessor is contained within the outer casing;
a transmitter to transmit a signal to a gearshift interlock relay of a motorized vehicle when the blood glucose concentration measurement is outside of the predetermined blood glucose concentration range or the blood glucose concentration measurement time is outside of the predetermined time range, the transmitted signal to prevent gear shifting and to immobilize the motorized vehicle without disabling ignition of the motorized vehicle, wherein the transmitter is contained within the outer casing; and
an operator interface that is configured to receive input directly from an operator, wherein the operator interface is integrated with the outer casing;
wherein the outer casing is separate and distinct from the motorized vehicle.

2. A motorized vehicle controller, comprising:
an outer casing;
a receiver to receive blood glucose concentration data, wherein the receiver is contained within the outer casing;
processing logic to compare the blood glucose concentration data to a predetermined blood glucose concentration range, the processing logic to further determine whether the blood glucose concentration data is within the predetermined blood glucose concentration range, wherein the processing logic is contained within the outer casing;
a transmitter to transmit a signal to a gearshift interlock relay of a motorized vehicle in response to determining whether the blood glucose concentration data is within the predetermined blood glucose concentration range, wherein the transmitter is contained within the outer casing; and
an operator interface that is configured to receive input directly from an operator, wherein the operator interface is integrated with the outer casing,
wherein the outer casing is separate and distinct from the motorized vehicle.

3. The controller of claim 2:
the receiver to further receive a blood glucose concentration measurement time; and
the processing logic to further compare the blood glucose concentration measurement time to a predetermined time range and determine whether the blood glucose measurement time is within the predetermined time range.

4. The controller of claim 2, the transmitter to further transmit the signal to the gearshift interlock relay through a telematic motor vehicle service in response to determining whether the blood glucose concentration data is within the predetermined blood glucose concentration range and determining whether the blood glucose concentration measurement time is within the predetermined time range.

5. The controller of claim 2, the transmitter to further transmit the signal wirelessly to the gearshift interlock relay in response to determining whether the blood glucose concentration data is within the predetermined blood glucose concentration range and determining whether the blood glucose concentration measurement time is within the predetermined time range.

6. The controller of claim 2, the transmitter to further transmit the signal to the gearshift interlock relay through a physical communication device in response to determining whether the blood glucose concentration data is within the predetermined blood glucose concentration range and determining whether the blood glucose concentration measurement time is within the predetermined time range, the physical communication device being selected from the group consisting of:
a data wire;
a data cable;
an optical fiber; and
universal serial bus tether.

7. The controller of claim 2, the transmitter to further transmit a signal that locks a gearshift and immobilizes the motorized vehicle without disabling ignition in response to the blood glucose concentration data being outside of the predetermined blood glucose concentration range.

8. The controller of claim 2, the transmitter to further transmit a signal that locks a gearshift and immobilizes the motorized vehicle without disabling ignition in response to the blood glucose concentration measurement time being outside of the predetermined time range.

9. The controller of claim 2, the transmitter to further transmit a signal that unlocks a gearshift in response to the blood glucose concentration data being within the predetermined blood glucose concentration range.

10. The controller of claim 9, the transmitter to further transmit a signal that unlocks a gearshift in response to the blood glucose concentration measurement time being within the predetermined time range.

11. The controller of claim 2, the processing logic comprising a computer readable medium.

12. The controller of claim 2, the processing logic comprising a microprocessor.

13. The controller of claim 2, the processing logic comprising a mobile application.

14. The controller of claim 2, wherein the controller is configured for after-market installation on a motorized vehicle.

* * * * *